(12) United States Patent
Hvichia

(10) Patent No.: US 7,993,908 B2
(45) Date of Patent: Aug. 9, 2011

(54) MICROSTRUCTURE FOR PARTICLE AND CELL SEPARATION, IDENTIFICATION, SORTING, AND MANIPULATION

(75) Inventor: Georgi Hvichia, Philadelphia, PA (US)

(73) Assignee: Parsortix, Inc., Philadelphia, PA (US)

( * ) Notice: Subject to any disclaimer, the term of this patent is extended or adjusted under 35 U.S.C. 154(b) by 1576 days.

(21) Appl. No.: 10/587,053

(22) PCT Filed: Jul. 17, 2002

(86) PCT No.: PCT/US02/22689
§ 371 (c)(1),
(2), (4) Date: Dec. 11, 2006

(87) PCT Pub. No.: WO03/008931
PCT Pub. Date: Jan. 30, 2003

(65) Prior Publication Data
US 2007/0072290 A1 Mar. 29, 2007

Related U.S. Application Data

(60) Provisional application No. 60/306,296, filed on Jul. 17, 2001.

(51) Int. Cl.
*C12M 1/34* (2006.01)
(52) U.S. Cl. ............... 435/287.2; 435/288.7; 435/297.2; 435/308.1; 422/534; 422/73; 436/63
(58) Field of Classification Search .............. 435/287.2, 435/288.5, 293.1, 297.2; 422/534, 73; 436/63
See application file for complete search history.

(56) References Cited

U.S. PATENT DOCUMENTS

| | | | |
|---|---|---|---|
| 5,023,054 A | 6/1991 | Sato | |
| 5,089,384 A * | 2/1992 | Hale | 435/173.4 |
| 5,486,335 A | 1/1996 | Wilding | |
| 5,728,581 A | 3/1998 | Schwartz et al. | |
| 5,837,115 A | 11/1998 | Austin | |
| 5,866,345 A | 2/1999 | Wilding | |
| 6,004,821 A | 12/1999 | Levine et al. | |
| 6,008,040 A | 12/1999 | Datar | |
| 6,184,029 B1 | 2/2001 | Wilding | |
| 6,783,928 B2 * | 8/2004 | Hvichia et al. | 435/2 |
| 2007/0072290 A1 | 3/2007 | Hvichia | |
| 2007/0172903 A1 | 7/2007 | Toner et al. | |

FOREIGN PATENT DOCUMENTS
WO 2006078470 A2 7/2006
* cited by examiner

*Primary Examiner* — William H Beisner
(74) *Attorney, Agent, or Firm* — Dilworth Paxson LLP; Gary D. Colby

(57) ABSTRACT

The invention relates to microscale cell separating apparatus which are able to separate cells on the basis of size of the cells, interaction of the cells with surfaces of the apparatus, or both. The apparatus comprises a stepped or sloped separation element (16) interposed between an inlet region (20) and an outlet region (22) of a void that can be filled with fluid. The void can be enclosed within a cover (12) and fluid flow through the void engages cells with the separation element. Only cells which have (or can deform to have) a characteristic dimension smaller than or equal to the distance between a step and the cover or body can pass onto or past a step. Modifications of surfaces within the apparatus can also inhibit passage of cells onto or past a step.

33 Claims, 2 Drawing Sheets

MICROSTRUCTURE FOR PARTICLE AND CELL SEPARATION, IDENTIFICATION, SORTING, AND MANIPULATION

CROSS-REFERENCES TO RELATED APPLICATIONS

This application is a national phase application of International Application No. PCT/US02/22689, filed 17 Jul. 2002, which is now inactive, and is entitled to priority pursuant to 35 U.S.C. §119(e) to U.S. provisional patent applications No. 60/306,296, which was filed on 17 Jul. 2001.

BACKGROUND OF THE INVENTION

Developments in methods of manufacturing very small devices, such as microelectronic devices, have made it possible to precisely and reproducibly make devices having features with nanometer-scale dimensions. Apart from use of such methods in microelectronic device production, similar technology has been used to make devices for handling biological materials, such as cells and macromolecules.

Microengineered bio-handling devices having structural elements with minimal dimensions ranging from tens of micrometers (the dimensions of biological cells) to nanometers (the dimensions of some biological macromolecules) have been described. This range of dimensions (nanometers to tens of micrometers) is referred to herein as "microscale." For example, U.S. Pat. No. 5,928,880, U.S. Pat. No. 5,866,345, U.S. Pat. No. 5,744,366, U.S. Pat. No. 5,486,335, and U.S. Pat. No. 5,427,946 describe microscale devices for handling cells and biological molecules.

Hemocytometry is a field of medical analysis and research wherein blood cells are analyzed using variety of techniques and devices. Basic manually-operated devices such as microscope slides with Neubauer or Makler chambers were developed over a century ago. These devices are expensive, reusable, and lack flexibility, multiple features, and disposability. Disposability is especially desirable to minimize medical personnel interaction with potentially hazardous biological specimens.

Every year, approximately 500,000 patients are diagnosed with blood disorders worldwide, including about 30,000 per year in the United States. Many blood disorders can be alleviated by transplantation of stem cells (i.e., relatively non-differentiated cells which retain at least hematopoietic capacity) into the patient. The ideal source of stem cells is the same patient to whom the cells are to be administered. However, hematopoietic (and other) stem cells are relatively rare in adults, and can be difficult to isolate in large numbers.

Blood drawn from the umbilicus shortly after delivery ("cord blood") is a rich source of hematopoietic stem cells. Cord blood storage methods are presently known and used commercially, but have the drawback that a relatively large volume (e.g., 100 to 250 milliliters) of blood must be stored in order to preserve a sufficient number of hematopoietic stem cells for use in future medical procedures. The large volume of cord blood that is stored increases the cost and decreases the convenience of the procedure. The stored volume could be decreased significantly (e.g., to 0.1 to 1 milliliter) if stem cells could be separated from cord blood prior to storage. However, present methods of separating stem cells from cord blood are expensive and cumbersome and are sometimes ineffective. The present invention overcomes the shortcomings of previously known stem cell separation methods and facilitates efficient and cost-effective separation of stem cells from cord blood.

BRIEF SUMMARY OF THE INVENTION

The invention relates to a microscale apparatus for separating cells. The apparatus comprises a body, a cover, and a separation element. The body defines a void having inlet and outlet regions. A separation region is interposed between the inlet and outlet regions. The cover contacts the body and covers at least the separation region of the void. The separation element is disposed in the separation region of the void and contacts either the body or the cover. The separation element has a plurality of flat portions that are disposed at different distances from the cover or body (respectively) to form steps or ramps. The highest step, the walls of the void (i.e., the body) and the cover or body (depending on the configuration) define a narrow passageway through which fluid can pass from the inlet region to the outlet region. The separation element can be attached to, or integral with, either the body or the cover. The cover or the body can define one or more (preferably at least two) fluid ports for providing liquid to, and withdrawing liquid from, the void. Preferably, the cover, body, or both, define a fluid inlet port in fluid communication with the inlet region and a fluid outlet port in fluid communication with the outlet region. A fluid displacement device can be attached to one or both of the ports for providing fluid to the fluid inlet port, withdrawing fluid from the fluid outlet port, or both. Separate fluid handling devices can be attached to each of the inlet and outlet ports.

The height of the narrow passageway, measured from the separation element to the cover, depends on the characteristic dimensions of the cells or particles that are to be retained or not to be retained. For the apparatus described herein, the height of the narrow passageway is generally in the range from 0.1 to 1000 micrometers (preferably in the range from 0.5 micrometer to 25 micrometers for animal or plant cells, or in the range 0.5 to 1.5 micrometers for bacteria).

The apparatus can have one or more fluid channels defined by the body, the cover, the separation element, or some combination of these. These fluid channels can be used to withdraw fluid from the void at a step of the separation element. The apparatus can also have a device for detecting a cell, a device for manipulating a cell, or a device for killing a cell (e.g., a heating element) in the void at a step of the separation element.

The apparatus can have a variety of surface modifications, such as an antibody attached to one or more of a surface of the separation element, a surface of the inlet region, a surface of the outlet region, and a surface of the cover.

A plurality of the apparatus can be connected in series or in parallel.

The invention also relates to a method of separating cells. The method comprises providing the cells to the inlet region of an apparatus of the type described herein and thereafter collecting cells from one of a step of the separation element, the outlet region, and the inlet region. Preferably, a fluid is passed from the inlet region to the outlet region after (and/or while) providing the cells to the inlet region, and the cells are collected from a step of the separation element. For example, the cells can be cells of a blood sample (e.g., a cord blood sample) and the collected cells can be stem cells. When a blood sample is used, the height of the narrow passageway is preferably sufficient to permit passage of blood platelets therethrough.

The invention also includes a kit for separating cells. The kit comprises the components of the apparatus described herein, and can further comprise instructions or reagents for using the apparatus.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. However, that the invention is not limited to the precise arrangements and instrumentalities shown.

DETAILED DESCRIPTION OF THE INVENTION

Figure 1:
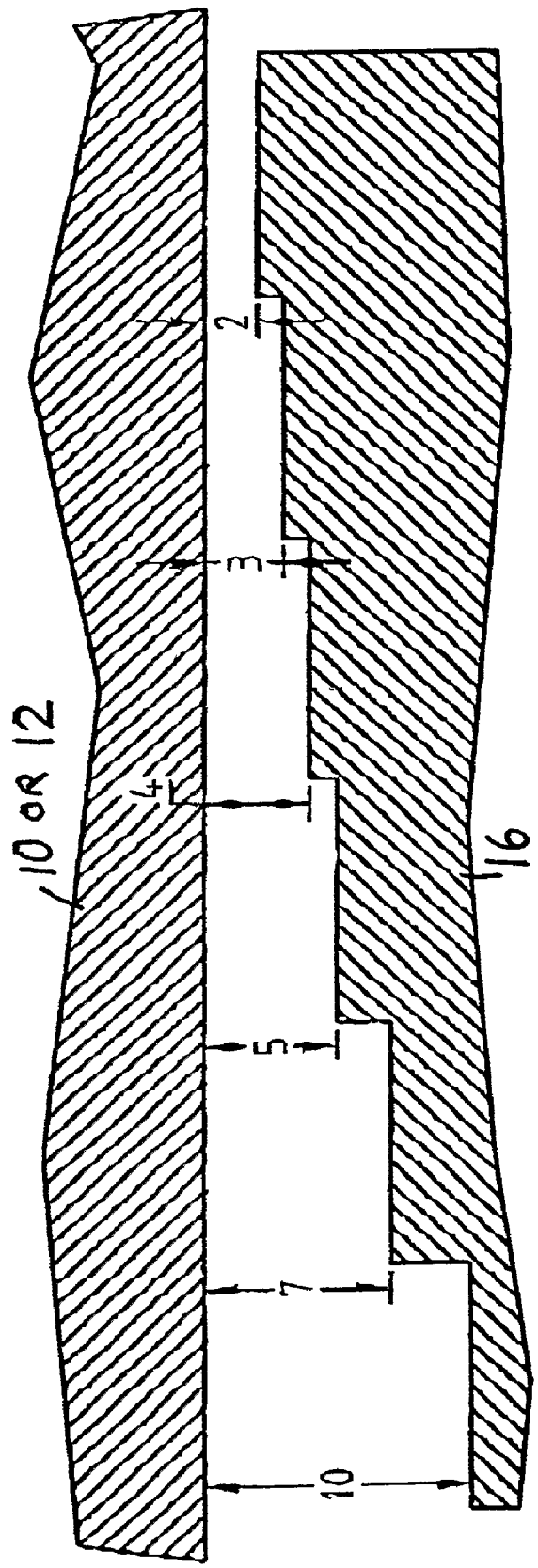
FIG. 1 is a cross section of a portion of the apparatus described herein, showing the stepped structure of the separation element. Numbers indicate relative distance between the separation element (16) and the cover (12) or body (10).

The invention relates to an apparatus for separating cells on the basis of one or both of their size and geometry. The apparatus comprises a body having a void therein. The void has an inlet region and an outlet region and can be filled with fluid. A separation element separates the inlet and outlet regions of the void and has at least two steps with characteristic heights. A cover is disposed across the void, and covers at least the portion of the void wherein the highest portion of the separation element occurs. Thus, fluid flow through the device passes from the inlet region, across and over the separation element, and into the outlet region.

In one embodiment, the cover is disposed across substantially the entire area of the void, yielding a closed fluid system. If fluid flow through the system is desired, the cover, the body, or both, can have inlet and an outlet ports. The ports can be simple holes which extend through the cover or body, or they can have fixtures (burrs, rings, hubs, or other fittings) associated with them for facilitating connection of a fluid handling device with the port. These ports facilitate addition and withdrawal of fluid and allow application of cells to the apparatus or collection of cells therefrom. By way of example, the body can be adapted to fit a peristaltic pump, a syringe pump, or substantially any other fluid displacement device by way of Luer-type fittings.

The shape, material, and construction of the body are not critical, except that the void in the body should be machined in such a way that a cover can be applied across the void in order to form a fluid-tight seal with the body around the edges of the void. Preferably, the void is formed in a flat portion of the body, and a flat cover is used that has a size and shape sufficient to completely cover the void.

Similarly, the shape, material, and construction of the cover are not critical, except that the cover should form a fluid-tight seal with the body at the edges of the void and should extend from the body at one edge of the void, along the highest portion of the separation element across the void, to the body at another edge of the void, thereby defining (with the separation element) a narrow passageway through which liquid must flow in order to pass from the inlet region to the outlet region of the void.

The cover can be movable, bendable, or deflectable, in order to change the size (i.e., height) and shape of the narrow passageway if desired. Any of a variety of mechanical apparatus can be used to accomplish movement of the cover (e.g., controllably movable brackets having an inclined plane upon which the cover rests, so that the cover can be lifted or lowered as desired). Alternatively, the cover can have a bimetallic construction, so that upon heating or applying an electrical potential to the two metals, the cover bends. The direction of the bend can be predicted using, for example, the thermal expansion coefficients of the two metals, and a bimetallic cover can be arranged so that it decreases or increases the size of the narrow passageway based on the temperature at which it is maintained. As another alternative, the cover can be manufactured from any of a variety of known piezoelectric materials. Application of electrical potential to a piezoelectric material induces deformation (i.e., bending) of the material in ways that are predictable, depending on the identity of the material.

The separation element has a 'stepped' structure with at least two steps. One of the steps is the highest. The separation element can be attached to (or integral with) either the body or the cover, or it can be a separate piece of material sandwiched between the body and the cover. When the device is assembled, the steps of the separation element define selected distances between the separation element and either the body (i.e., the surface of the void in the body) or the cover. Assessed in the direction from the inlet region of the void toward the outlet region of the void, the distance between the steps and the body or cover decreases. Thus, movement of cells suspended in a fluid flowing through the assembled apparatus can be inhibited or halted at a step that is characteristic of a dimension of the cell (e.g., the diameter of a substantially spherical cell or the rotational diameter of an irregularly-shaped cell).

In the same manner, substantially any particles that have characteristic dimensions on the same order as the distance between the steps and the cover or body can be separated using the apparatus. For example, bacteria can be sorted and separated using an apparatus that has a separation element that has steps disposed from the cover or body in increments of tenths of micrometers (e.g., 0.5 to 1.5 micrometers). Similarly, mineral particles and other small inanimate objects can be sorted using apparatus comprising a separation elements having steps which vary on the order of a characteristic dimension of the objects. Known fabrication techniques enable fabrication of steps which vary by tenths of micrometers to thousands of micrometers. At a micrometer scale, as preferred for the apparatus described herein, the height of the narrow passage is generally not more than 1 millimeter, and the steps vary in height by tenths of micrometers, micrometers, tens of micrometers, hundreds of micrometers, or combinations of these (e.g., see FIG. 2).

Cells which have a characteristic dimension that is smaller than the height of the narrow passageway will pass through the device from the inlet region to the outlet region. Likewise, cells which are capable of deforming to fit through the narrow passageway can pass from the inlet region to the outlet region. If the separation element has multiple steps, then movement of cells through the apparatus will be halted at a step that is separated from the cover or body by a distance that is smaller than a characteristic dimension of the cell. Using such a separation element, cells of several different types can be concentrated at different portions of the apparatus.

Figure 2:
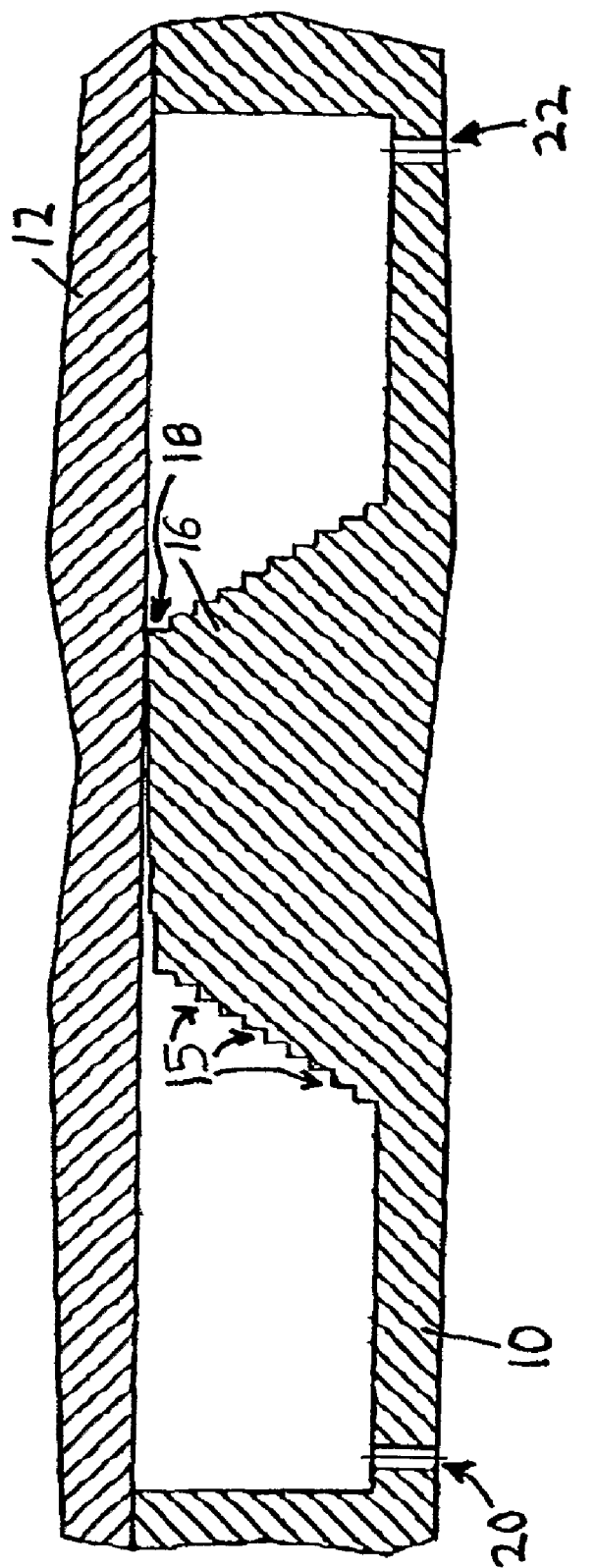
FIG. 2 is a cross section of an example of an assembled apparatus described herein, wherein the separation element (16) is integral with the body (10), has steps on both the face facing the inlet region and the face facing the outlet region, and has steps (15) of various heights. A narrow passageway (18) exists between the highest step and the cover (12). An inlet port (20) and an outlet port (22) are shown.

The steps of the separation element can be discrete steps, as illustrated in FIG. 1. Alternatively, one or more of the steps can be sloped, the steps being separated from one another by a flat portion that extends in the direction from the inlet region toward the outlet region. The length (in the direction of fluid flow) of the flat portion is not critical. However, where cells having a particular characteristic dimension are anticipated to be applied to the device, it can be preferable to include a relatively long flat portion before the first step that is expected to inhibit or prevent flow of the cells with the fluid, so that the cells can accumulate on that step. The flat portions of different steps can have the same length, or they can have different lengths, as illustrated in FIG. 2.

The heights of the steps can be selected based on the expected characteristic dimensions of cells in samples of a type intended to be applied to the apparatus. Alternatively, the heights of the steps can be selected arbitrarily. Thus, steps can differ in height by as little as 1 or a few nanometers or by as much as a few, several, or even tens of micrometers. The steps must occur on the face of the separation element that faces the inlet region of the void, so that cells moving from the inlet region toward the outlet region must traverse the steps. The steps can also occur on the face of the separation element that faces the outlet region of the void if this facilitates manufacture of the apparatus, or so that the apparatus can be used in either an inlet-to-outlet or outlet-to-inlet flow configuration. When the separation element has steps on the face that faces the outlet region, then cells which pass through the narrow passageway can be sorted on the trailing edge of the separation element. For example, many cells exhibit at least limited deformability, and some cells will often pass through the narrow passageway even though their characteristic dimensions indicate that they should not (i.e., some cells which appear too large to pass through the narrow passageway nonetheless pass). If these cells settle on a step on the outlet side of the separation element, then they can be collected, detected, observed, ablated, or manipulated, as with cells on a step on the inlet face of the separation element.

The body, the cover, or both, can have one or more fluid channels that fluidly connect with the surface of a step of the separation element, for removing fluid from the step (including any cells suspended in the fluid upon that step). Furthermore, when the step has discrete grooves or regions in the step, the cover or body can be machined so that the fluid channels fluidly communicate most nearly with a discrete groove or region upon the step, for removing fluid in the vicinity of that groove or region of the step. Likewise, the body, the cover, the separation element, or some combination of these, can have an optical, electrical, or optico-electrical device constructed therein or thereon (e.g., by etching, film deposition, or other known techniques) at a position that corresponds to a selected step or a selected groove or region of a step. Such devices can be used to detect cells (e.g., using a detector to detect a decrease in light or other radiation transmitted across the fluid between the surface of the step and the cover or body) or to manipulate cells (e.g., using an activatable heating element to ablate cells which pass or rest near the heating element). Devices constructed upon the cover, the body, or the steps can be made individually activatable by assigning an electronic address to the device. In this manner, cells can be detected at discrete areas of the device, and cells at selected areas can be manipulated without manipulating cells at other positions.

Harvesting of cells from a selected step (or a plurality of selected steps) can be performed by simply withdrawing fluid from that step or a portion of the step. In some instances, such as when adhesion between cells and a step upon which they rest occurs, it can be advantageous to apply energy to the apparatus in order to dislodge the cells or otherwise facilitate their removal. The energy can be applied in many forms, and a preferable form will usually depend on the type of cell or object to be displaced and the identity of the force or phenomenon which inhibits removal of the cell or object from the step. By way of example, withdrawal of fluid from one portion of a step can be performed simultaneously with addition of fluid at another portion of the same step. Other examples of forms in which energy can be applied to the apparatus in order to harvest cells include shaking, tapping, or vibrating the apparatus, or applying energy in the form of ultrasound, heat, infrared or other radiation, bubbles, compressed air, and the like.

Instead of recovering cells that are retained on one or more steps of the separation element, the cells can instead be detected or manipulated. In one embodiment, one or more cells are lysed by application to the cells of electrical, mechanical, or heat energy, thereby releasing the contents of the cell in the void of the apparatus. The cell contents can be analyzed or manipulated in the apparatus, or they can be recovered from the apparatus and analyzed or manipulated outside of the apparatus. By way of example, a cell that is retained at a particular location on a step can be lysed using a device located at that particular location, thereby releasing the cell's DNA into the void. The DNA can be amplified in the void by providing PCR reagents to the void, or it can be collected (e.g., by passing fluid through the void and collecting the DNA in the outlet fluid) and amplified outside of the apparatus. The apparatus can thus be used to analyze the contents of individual cells or groups of cells.

When the apparatus is filled with fluid, the fluid fills the void, including the inlet and outlet regions, and completely covers the separation element. If desired, the apparatus can be lightly manipulated (e.g., by tapping or shaking), or the fluid can be applied under pressure, in order to ensure that all portions of the void are filled with the fluid and to remove any air bubbles that may be present. Air bubbles, if present, can also be removed by passing fluid from the inlet region to the outlet region.

The body, cover, and separation element can be constructed from substantially any material that will hold its shape during operation of the apparatus as described herein. However, rigid materials are preferred. Examples of suitable materials include various glasses, solid polymers, and crystalline minerals. Silicon is a preferred substrate material because of the well-developed technology permitting its precise and efficient fabrication, but other materials can be used, including various glasses and cast, molded, or machined polymers including polytetrafluoroethylenes. The inlet and outlet ports, the separation element, and the surfaces defining the void in the body can be fabricated inexpensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, precision machining methods, or etching methods which may be performed by either wet chemical processes or plasma processes. (See, e.g., Manz et al., 1991, Trends in Analytical Chemistry, 10:144-149).

Steps of varying widths and heights can be fabricated with microscale dimensions for separating cells in a sample. A silicon substrate containing a fabricated steps can be covered and sealed (e.g., anodically bonded) with a thin glass cover. Other clear or opaque cover materials may be used. Alternatively, two silicon substrates can be sandwiched, or a silicon substrate can be sandwiched between two glass covers. Preferably, at least one of the body and the cover is transparent. Use of a transparent material facilitates dynamic viewing of the contents of the device, and allows probing of fluid flow in the apparatus, either visually or by machine. Other fabrication approaches can be used.

One advantage of the apparatus described herein is that they can be manufactured in a wide variety of sizes and geometrical arrangements, depending on the intended use of the apparatus. In addition, multiple apparatus can be manufactured on or in a single piece of material, such as a unitary silicon block or a microscope slide. Furthermore, the multiple apparatus on a slide can be connected in series, in parallel, or both. By way of example, several apparatus having a narrow passageway of relatively small height (e.g., 2 micrometers) can be constructed on a single block of material, and a sample (e.g., cord blood) can be fed to the inlet region of each of those apparatus. By feeding fluid through the apparatus, platelets and small cell debris can be removed from the sample. Stem cells and red and white blood cells will be retained in the inlet region or on the steps.

After platelets have been removed, the flow in the apparatus can be reversed, and the retained cells can be transferred (directly, by way of fluid circuit switching, or indirectly, by manually or automatically collecting the cells and reapplying them) to the inlet region of one or more second apparatus. These second apparatus can, but need not, be made in the same piece of material as the first series of apparatus. These second apparatus comprise a separation element that separates stem cells from red blood cells based on their different characteristic dimensions.

By feeding fluid through the second apparatus, red blood cells are separated from stem cells. If desired, the narrow passageway of the second apparatus can have dimensions that permit passage therethrough of the red blood cells. Stem cells can be collected from the second apparatus, for example by way of a fluid channel machined into the body at a position where accumulation of stem cells is anticipated. If desired, the collected stem cells can be provided to the inlet region of a third apparatus which comprises a separation element having a cell-type specific antibody attached to one or more steps thereof (or a portion of one or more steps), in order to separate stem cells from remaining non-stem cells, or to separate different classes of stem cells.

The capacity of the apparatus described herein depends on the number of cells that can occupy a step of the separation element without occluding or severely limiting fluid flow. Because passage of a cell past a step of the separation element depends primarily upon the distance between the step and the cover or body, the width of the step (and thus the width of the narrow passageway) is not critical. Advantageously, the steps can be made very wide or many steps can be arranged in parallel. Thus, if one portion of a step becomes clogged with cells that cannot fit in the space between the step and the cover or body, fluid flow can continue along the remaining width of the step. In one embodiment, the steps are arranged concentrically in a circular, oval, rippled or irregular form, so that the width of steps upon which cell accumulation is anticipated can be maximized.

The surfaces of the apparatus can be chemically treated or coated with any of a variety of known materials which reduce or enhance agglutination of cells with the material selected for the cover, body, or obstacles. By way of example, an antibody which binds specifically with a cell-surface antigen can be attached to a surface of the void using any of a variety of protein anchoring chemistries, a surface of a step, or a surface of the cover, in order to inhibit passage of cells which exhibit the antigen past the surface (e.g., in order to differentiate cells of similar size but different type). The surfaces of the apparatus can also be treated with any of a variety of known reagents (e.g., oxygen plasma) in order to increase the hydrophilicity of the surfaces. This treatment can improve the rate and completeness of filling of the apparatus with a fluid medium introduced into the apparatus.

The assembled apparatus can be used to separate cells by providing cells to the inlet region of the void. If the cells are motile, then they can distribute themselves on the steps of the separation element. More typically, however, the apparatus will be used by applying a fluid flow between the inlet and outlet regions of the void (e.g., by way of fluid ports fluidly connected with each). Cells can be provided to the inlet region in fluid flowing through the apparatus, by a separate port, or by providing the cells to the region prior to applying the cover to the body. Fluid flow carries or pushes the cells in the direction from the inlet region toward the separation element. If a cell has a characteristic dimension smaller than or equal to the distance between the first step and the cover or body, then the cell can be carried onto the first step. Similarly, if the characteristic dimension of the cell is smaller than or equal to the distance between the next step and the cover or body, then the cell can be carried onto the next step. If the cell encounters a step for which the distance between the step and the step and the cover or body is smaller than the characteristic dimension of the cell, then the cell cannot pass onto the step unless the cell can deform to fit through the gap. Cells that are retained on a step can be collected or manipulated using fluid channels or devices that are addressed to the particular step.

In one embodiment, the apparatus is made to separate stem cells from other cells in a blood sample (e.g., a cord blood sample). Stem cells are generally larger (70% have a characteristic dimension of about 12-16 micrometers) than red blood cells (which are flat bi-concave disc-shaped cells having characteristic dimensions of about 5.5 to 8.5 micrometers in diameter and 1.2-1.9 micrometers thick) or platelets (characteristic dimension=about 1 micrometer). This same apparatus can be used to separate fetal cells from its mother's peripheral blood cells in order to analyze the fetal cells (e.g., for indications of likely birth defects). Fetal cells are known to circulate in the mother's bloodstream.

If a device is used in which the height of the narrow passageway is more than about 1 micrometer, then most platelets will pass through the device without being retained on the separation element. If the height of the narrow passageway is about 2-5 micrometers, then most red blood cells, white blood cells, and stem cells will be retained on one or more steps of the separation element. If the separation element includes steps that are sufficiently distant (e.g., 2 to 10 micrometers) from the cover or body to permit red blood cells to pass upon the step, but which are not sufficiently distant to permit stem cells to pass upon the step, then the stem cells will be separated from the red blood cells.

If the width, length, or both, of steps which accommodate red blood cells are sufficiently great, then substantially all red blood cells in the applied sample can be collected on those steps, and substantially all stem cells will be excluded from those steps and will remain in the inlet region or at steps having a greater distance between the step and cover or body (e.g., more than 12 micrometers). Collection of fluid from the inlet region or from one or more steps which accommodate stem cells can result in isolation of the stem cells from red blood cells of the blood sample. The collected stem cells can be centrifuged, ultrafiltered, or otherwise compacted into a form convenient for storage.

The net effect of this procedure can be to dramatically reduce the volume of the blood sample which must be stored in order to store the stem cells contained therein. This procedure also isolates the stem cells from red blood cells and from iron-containing compounds (e.g., proteins such as ferritin and hemoglobin) that could potentially harm the stem cells or induce an immune response in a recipient of the blood sample.

The cover, body, and separation element (if not already connected to one of the cover and body) can be provided in the form of a kit to be assembled by the user (e.g., after adding a fluid medium to the void in the body). The kit can also include instructions for using the apparatus or reagents to be used therewith. The apparatus can be supplied pre-filled with fluid.

The apparatus can have indicia associated in a fixed position with respect to the separation element. The indicia can be used to assess whether cells having a selected characteristic (e.g., size or ability to bind with an antibody fixed to a surface of the apparatus) are being retained in the apparatus. The indicia can be printed, painted, or stamped on, or engraved or etched in the body or the cover, preferably on a surface of a component that is transparent, so that the indicia and the cells in the apparatus can be simultaneously observed by a user. The indicia preferably do not alter the shape, diameter, or smoothness of the fluid path with which they are associated. For example, the indicia can be on or in the opposite face of a transparent material in which the fluid path exists. Alternatively, the indicia can be on or in one face of a transparent material that has a different face opposed against the fluid path (e.g., the exterior face of the cover).

It will be appreciated by those skilled in the art that changes could be made to the embodiments described above without departing from the broad inventive concept thereof. It is understood, therefore, that this invention is not limited to the particular embodiments disclosed, but covers modifications within the spirit and scope of the present invention as defined by the appended claims.

What is claimed is:

1. A microscale apparatus for separating particles, the apparatus comprising a body, a cover, and a separation element,
    the body and cover defining a void having an inlet region, an outlet region, and a surface,
    the separation element i) being disposed in the void, ii) having a plurality of steps including a first step and a second step, and iii) defining a narrow passageway that fluidly connects the inlet and outlet regions in a fluid path,
    the narrow passageway including a first passageway and a second passageway,
    the first passageway fluidly connecting the inlet region and the second passageway, being bounded by the first step and the surface of the void, and having a height defined by the distance between the first step and the surface of the void, and
    the second passageway fluidly connecting the first passageway and the outlet region, being bounded by the second step and the surface of the void, and having a height defined by the distance between the second step and the surface of the void, wherein the width of the narrow passageway at the portion of the second step nearest the inlet region in the fluid path is greater than the height of the second passageway,
    the height of the second passageway being smaller than the height of the first passageway.

2. The apparatus of claim 1, wherein the separation element is attached to at least one of the body and the cover.

3. The apparatus of claim 2, wherein the separation element is integral with at least one of the body and the cover.

4. The apparatus of claim 1, wherein one of the cover and the body defines a fluid inlet port in fluid communication with the inlet region and one of the cover and the body defines a fluid outlet port in fluid communication with the outlet region.

5. The apparatus of claim 4, further comprising a fluid displacement device for providing fluid to the fluid inlet port.

6. The apparatus of claim 1, wherein the void is filled with fluid.

7. The apparatus of claim 6, wherein the particles are cells and the cells are disposed in the inlet region.

8. The apparatus of claim 1, wherein the height of each of the first and second passageways is in the range from 0.1 micrometer to 1000 micrometers.

9. The apparatus of claim 8, wherein the height of each of the first and second passageways is in the range from 0.5 micrometer to 25 micrometers.

10. The apparatus of claim 8, wherein the height of each of the first and second passageways is in the range from 1 micrometer to 16 micrometers.

11. The apparatus of claim 8, wherein the height of each of the first and second passageways is in the range from 1 micrometer to 10 micrometers.

12. The apparatus of claim 8, wherein the height of each of the first and second passageways is in the range from 1 micrometer to 5 micrometers.

13. The apparatus of claim 1, wherein one of the body, the cover, and the separation element defines a fluid channel for withdrawing fluid from the void at a step of the separation element.

14. The apparatus of claim 1, further comprising a device for detecting a particle in the void at a step of the separation element.

15. The apparatus of claim 1, further comprising a device for manipulating a particle in the void at a step of the separation element.

16. The apparatus of claim 15, wherein the device is a device for killing a cell.

17. The apparatus of claim 16, wherein the device is a heating element.

18. The apparatus of claim 1, wherein a surface of the separation element has an antibody attached thereto.

19. An apparatus comprising two apparatus of claim 1, wherein the outlet region of the first apparatus is in fluid communication with the inlet region of the second apparatus.

20. The apparatus of claim 1, wherein each of the first step and the second step is defined by a pair of planar surfaces of the separation element that meet at a right angle.

21. The apparatus of claim 1, wherein the separation element has at least one additional step in addition to the first and second step, each additional step defining an additional passageway that i) fluidly connects the second step and the outlet region ii) is bounded by the additional step and the surface of the void, and iii) has a height defined by the distance between the additional step and the surface of the void, the height of each additional passageway being smaller than the height of all other passageways between it and the inlet region.

22. The apparatus of claim 1, wherein the height of the first passageway is about 12-16 micrometers and the height of the second passageway is about 5.5 to 8.5 micrometers.

23. A kit comprising a body, a cover, and a separation element,
    the body and cover being adapted to fit one another and, when assembled, to define a void having an inlet region, an outlet region, and a surface, the separation element i) being disposable in the void of the assembled body and cover, ii) having a plurality of steps including a first step and a second step, and iii) defining a narrow passageway that fluidly connects the inlet and outlet regions in a fluid path when the body and cover are assembled with the separation element disposed in the void such that, the narrow passageway includes a first passageway and a second passageway, the first passageway fluidly connecting the inlet region and the second passageway, being bounded by the first step and the surface of the void, and having a height defined by the distance between the first step and the surface of the void, and the second passageway fluidly connecting the first passageway and the outlet region, being bounded by the second step and the surface of the void, and having a height defined by the distance between the second step and the surface of the void, wherein the width of the narrow passageway at the portion of the second step nearest the inlet region in the fluid path is greater than the height of the second passageway, the height of the second passageway being smaller than the height of the first passageway.

24. A method of separating particles, the method comprising providing the particles to the inlet region of a microscale apparatus, the apparatus comprising a body, a cover, and a separation element, the body and cover defining a void having an inlet region, an outlet region, and a surface, the separation element being disposed in the void, having a plurality of steps including a first step and a second step, and iii) defining a narrow passageway that fluidly connects the inlet and outlet regions in a fluid path, the narrow passageway including a first passageway and a second passageway, the first passageway fluidly connecting the inlet region and the second passageway, being bounded by the first step and the surface of the void, and having a height defined by the distance between the first step and the surface of the void, and the second passageway fluidly connecting the first passageway and the outlet region, being bounded by the second step and the surface of the void, and having a height defined by the distance between the second step and the surface of the void, wherein the width of the narrow passageway at the portion of the second step nearest the inlet region in the fluid path is greater than the height of the second passageway, the height of the second passageway being smaller than the height of the first passageway, passing a fluid from the inlet region into the outlet region by way of the narrow passageway, whereby particles are separated based on a characteristic dimension of the individual particles, and thereafter collecting separated particles.

25. The method of claim 24, wherein the fluid is passed from the inlet region to the outlet region using a fluid displacement device to add fluid to the inlet region by way of a fluid inlet port that extends through at least one of the body and the cover and that fluidly communicates with the inlet region.

26. The method of claim 24, wherein the separated particles are collected from a step of the separation element.

27. The method of claim 24, wherein the particles provided to the inlet region are cells of a blood sample and the collected particles are stem cells.

28. The method of claim 27, wherein the blood sample is a cord blood sample.

29. The method of claim 27, wherein the height of the second passageway is sufficient to permit passage of blood platelets therethrough.

30. The method of claim 24, wherein the particles are cells.

31. The method of claim 24, wherein the particles provided to the inlet region are cells of a blood sample obtained from a pregnant woman and the collected particles are fetal cells.

32. The method of claim 24, wherein the particles provided to the inlet region are cells of a blood sample obtained from a pregnant woman and the collected particles are fetal stem cells.

33. The method of claim 24, wherein the height of the first passageway is about 12-16 micrometers and the height of the second passageway is about 5.5 to 8.5 micrometers.

* * * * *